(12) United States Patent
Murray et al.

(10) Patent No.: US 7,083,610 B1
(45) Date of Patent: Aug. 1, 2006

(54) DEVICE FOR IRRADIATING TISSUE

(75) Inventors: Steven C. Murray, Santa Cruz, CA (US); Scott A. Davenport, Half Moon Bay, CA (US)

(73) Assignee: Laserscope, San Jose, CA (US)

( * ) Notice: Subject to any disclaimer, the term of this patent is extended or adjusted under 35 U.S.C. 154(b) by 0 days.

(21) Appl. No.: 09/589,675

(22) Filed: Jun. 7, 2000

(51) Int. Cl.
A61B 18/18 (2006.01)

(52) U.S. Cl. .............................. 606/9; 606/22; 607/88; 607/91

(58) Field of Classification Search .................... 606/8, 606/9, 13, 17, 22, 23; 607/88–91, 93, 100, 607/104; 372/69–71
See application file for complete search history.

(56) References Cited

U.S. PATENT DOCUMENTS

| | | | | |
|---|---|---|---|---|
| 4,273,109 A | * | 6/1981 | Enderby | 600/175 |
| 4,336,809 A | * | 6/1982 | Clark | 600/478 |
| 4,695,697 A | * | 9/1987 | Kosa | 219/121.83 |
| 4,764,739 A | * | 8/1988 | Salour | 332/751 |
| 4,852,567 A | * | 8/1989 | Sinofsky | 128/303.1 |
| 4,853,528 A | * | 8/1989 | Byren et al. | 250/203 |
| 4,994,059 A | * | 2/1991 | Kosa et al. | 606/12 |
| 5,405,368 A | * | 4/1995 | Eckhouse | 607/88 |
| 5,415,655 A | * | 5/1995 | Fuller et al. | 606/16 |
| 5,425,754 A | * | 6/1995 | Braun et al. | 607/88 |
| 5,720,772 A | * | 2/1998 | Eckhouse | 607/88 |
| 5,735,844 A | * | 4/1998 | Anderson et al. | 606/9 |
| 5,824,023 A | | 10/1998 | Anderson | 607/88 |
| 5,830,208 A | * | 11/1998 | Muller | 606/9 |
| 5,885,274 A | * | 3/1999 | Fullmer et al. | 606/9 |
| 5,928,222 A | * | 7/1999 | Kleinerman | 606/16 |
| 5,961,543 A | * | 10/1999 | Waldmann | 607/88 |
| 5,964,749 A | * | 10/1999 | Eckhouse et al. | 606/9 |
| RE36,634 E | * | 3/2000 | Ghaffari | 606/9 |
| 6,156,030 A | * | 12/2000 | Neev | 606/10 |
| 6,171,302 B1 | * | 1/2001 | Talpalriu et al. | 606/9 |
| 6,214,034 B1 | * | 4/2001 | Azar | 607/89 |
| 6,235,017 B1 | * | 5/2001 | Jegorv et al. | 606/16 |
| 6,254,594 B1 | * | 7/2001 | Berry | 606/2 |
| 6,270,492 B1 | * | 8/2001 | Sinofsky | 606/15 |
| 6,280,438 B1 | * | 8/2001 | Eckhouse et al. | 606/9 |
| 6,514,243 B1 | * | 2/2003 | Eckhouse et al. | 606/9 |
| 6,835,202 B1 | * | 12/2004 | Harth et al. | 607/91 |

OTHER PUBLICATIONS

"Aura. Greater Versatility, Reliability and Value" Product information available at: www.laserscope.com/professionals/aesthetics/aura.pdf.

* cited by examiner

*Primary Examiner*—A. Farah
(74) *Attorney, Agent, or Firm*—Haynes Beffel & Wolfeld LLP

(57) ABSTRACT

A device for irradiating tissue includes a fluorescent element for receiving pump radiation and responsively emitting radiation having different spectral characteristics than the pump radiation. A redirector receives emitted radiation promulgated in a direction away from a tissue target and redirects the radiation toward the target. The pump radiation may be supplied, for example, by a flashlamp or frequency-doubled neodymium-doped laser. Use of the device provides an inexpensive and effective alternative to conventional dye laser-based systems for various medical therapies, including treatment of vascular and pigmented lesions, tattoo and hair removal, and photodynamic therapy (PDT).

33 Claims, 5 Drawing Sheets

DEVICE FOR IRRADIATING TISSUE

FIELD OF THE INVENTION

The present invention relates generally to optical devices, and more particularly to devices for irradiating tissue for use in medical procedures.

BACKGROUND OF THE ART

A variety of medical procedures utilize a laser or other radiation source to irradiate a tissue target. Examples of such procedures include dermatological therapies such as treatment of vascular lesions and removal of tattoos and unwanted hair, as well as non-dermatological procedures such as photodynamic therapy (PDT) for treatment of tumors. In procedures involving irradiation of a tissue target, it is usually desirable to match the spectral characteristics of the light produced by the radiation source with the absorption characteristics of the target. This matching promotes efficient absorption of the radiation by the target (which is necessary to effect the localized heating or ablation of the target) and may minimize thermal damage to adjacent tissue.

To facilitate matching of the spectral characteristics of the radiation source with the absorption characteristics of the target, some medical procedures employ a dye laser as the radiation source. An example of one such dye laser is described in U.S. Pat. No. 5,066,293 to Furomoto ("Light Amplifier and Method of Photothermolysis"). The output wavelength of the dye laser is controlled by means of the choice of dye and/or adjustment of a tuning element such as an intracavity rotatable birefringent filter. Further, dye lasers are typically capable of delivering radiation having output energies and pulse durations suitable for a range of medical applications.

Disadvantages associated with dye lasers include their high expense and complexity. Misalignment of or damage to optical components, malfunctioning of the dye recirculation system, and/or problems with control circuitry may cause the tunable dye laser to become partially or fully inoperative, leading to downtime and substantial repair or replacement costs. Further, owing to their relative complexity, it may be necessary to provide extensive training and practice to clinicians before they are able to competently operate dye laser-based systems.

SUMMARY

According to one embodiment of the invention, a device for irradiating tissue is provided having a fluorescent element positioned to receive incident pump radiation. The fluorescent element may comprise, without limitation, a laser dye compound dispersed in a solid medium such as polyvinyl toluene, an encapsulated liquid dye solution, or a laser crystal such as ruby. Responsive to receipt of the incident pump radiation, the fluorescent element fluoresces and emits radiation having spectral characteristics substantially different from the spectral characteristics of the pump radiation.

Because the fluorescent element emits radiation in a diffuse manner, i.e., without a preferred direction, at least a portion of the emitted radiation travels in a direction away from the tissue target. The device is therefore provided with a redirector for redirecting toward the tissue target the portion of emitted radiation initially directed away from the target. In one embodiment, the redirector comprises a diffuse reflector having an elongated frustro-conical shape. Emitted radiation entering the redirector undergoes multiple reflections in a random-walk fashion and eventually exits the redirector travelling in the direction of the target. The device may be additionally provided with a transparent window having a first face positioned proximal the fluorescent element and a second face held in contact with the target. The window may be cooled to minimize thermal damage to tissue adjacent the target.

Devices of the foregoing description may be utilized to irradiate tissue for a number of medical procedures, including without limitation selective photothermolysis of vascular lesions, tattoo removal, treatment of wrinkles and stretch marks, and PDT. In practice, a clinician performing a procedure may simply select a device having a florescent element which emits radiation having spectral characteristics appropriate to the procedure and the absorption characteristics of the target tissue and connect the device to a source of pump radiation. Because the device utilizes fluorescence rather than lasing to generate the emitted radiation, the device can be manufactured inexpensively, is significantly less prone to malfunction, and is relatively easy to use when compared to prior art systems utilizing dye lasers.

BRIEF DESCRIPTION OF THE FIGURES

In the accompanying drawings:

FIG. 6(*b*) is a top plan view of an entrance face of the third embodiment.

DETAILED DESCRIPTION

Figure 1:
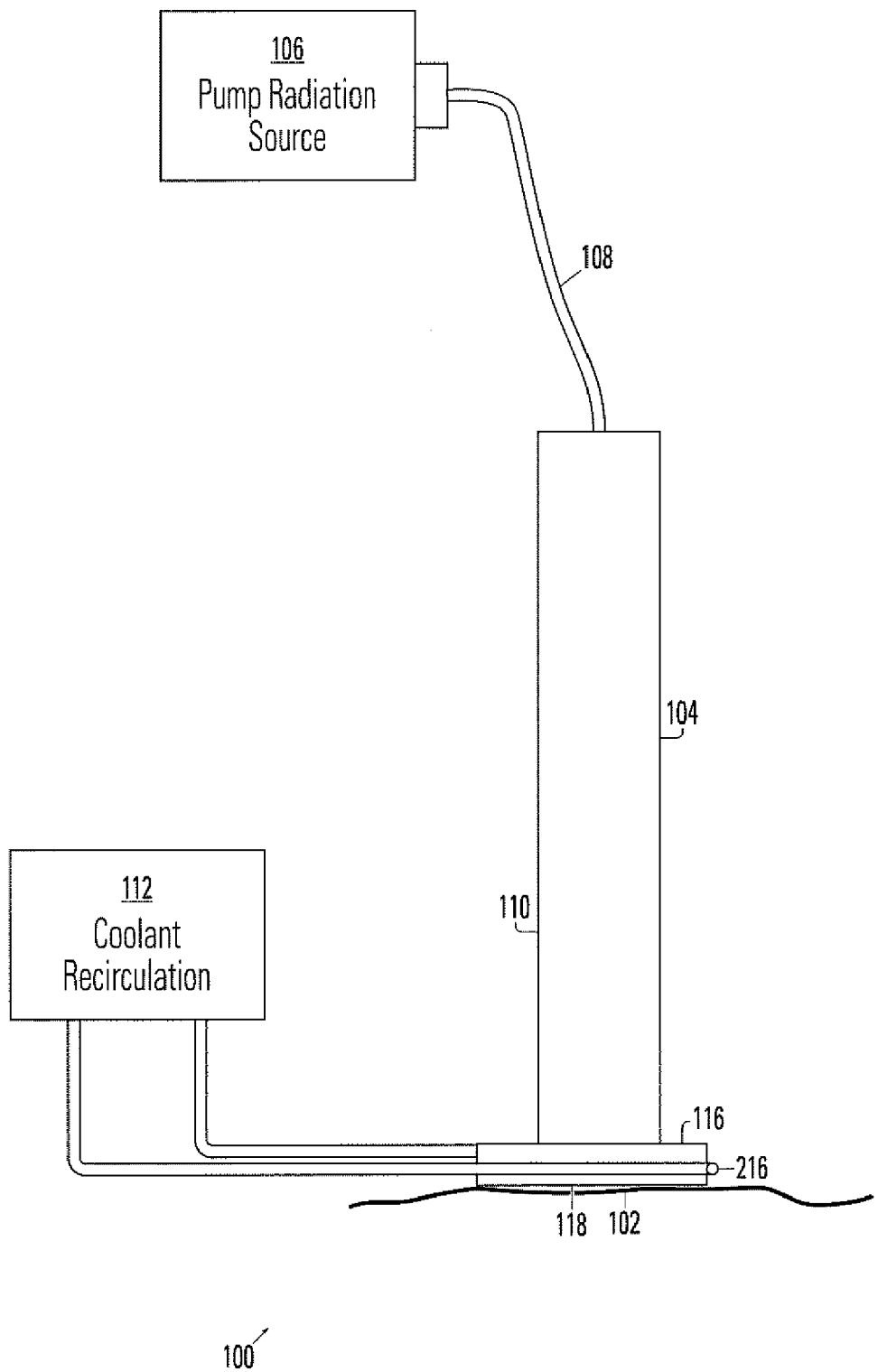
FIG. 1 is a system for irradiating tissue employing the fluorescent device of the present invention.

Referring initially to FIG. 1, there is depicted in block form a system 100 for irradiating a tissue target 102 utilizing a device 104 of the present invention. System 100 generally comprises a pump radiation source 106 configured to generate pump radiation and supply the pump radiation to device 104. Various light-emitting devices may be employed for pump radiation source 106 including, without limitation, a frequency-doubled neodymium-doped solid-state laser, an arc lamp or a flashlamp. In a typical mode of operation, pump radiation source 106 generates and supplies pulsed radiation having a wavelength of 532 nanometers and a pulse duration of between 0.1 and 500 milliseconds. Alternatively, pump radiation source 106 may generate CW or quasi-CW radiation. U.S. Pat. No. 5,151,909 to Davenport et al. ("Frequency Doubled Solid State Laser Having Programmable Pump Power Modes and Method for Controllable Lasers") describes an example of a Nd:YAG laser which may be utilized for pump radiation source 106.

Pump radiation source 106 is optically coupled to device 104 by optical fiber 108, which delivers the pump radiation to a fluorescent element (not shown in FIG. 1) held within a housing 110 of device 104. Optical fiber 108 is flexible and thereby allows device 104 to be freely positioned relative to pump radiation source 106. Alternatively, an articulated arm extending between pump radiation source 106 and device 104 may be utilized for optical coupling in place of optical fiber 108. In other embodiments of the invention, pump radiation source 106 may be integrated within housing 110 of device 104, obviating the need for optical fiber 108 or equivalent means of delivering the pump radiation.

System 100 may optionally include a coolant recirculation system 112 for removing heat from a window 116 of device 104. Window 116 is fabricated from an optically transparent material and has a distal face 118 which is held in thermal contact with tissue target 102 during operation of system 100. As is discussed further hereinbelow, cooling of window 116 beneficially reduces damage to non-targeted tissue and resultant scarring. Coolant recirculation system 112 will conventionally comprise heat exchanger-based or evaporative chiller for removing heat from a liquid coolant (which may consist of water or a water/glycol mix) and a pump for delivering the chilled coolant to thermally conductive tubing contacting surfaces of window 116. Other well-known techniques for cooling tissue target 102 may be substituted for or used in conjunction with coolant recirculation system 112.

Figure 2:
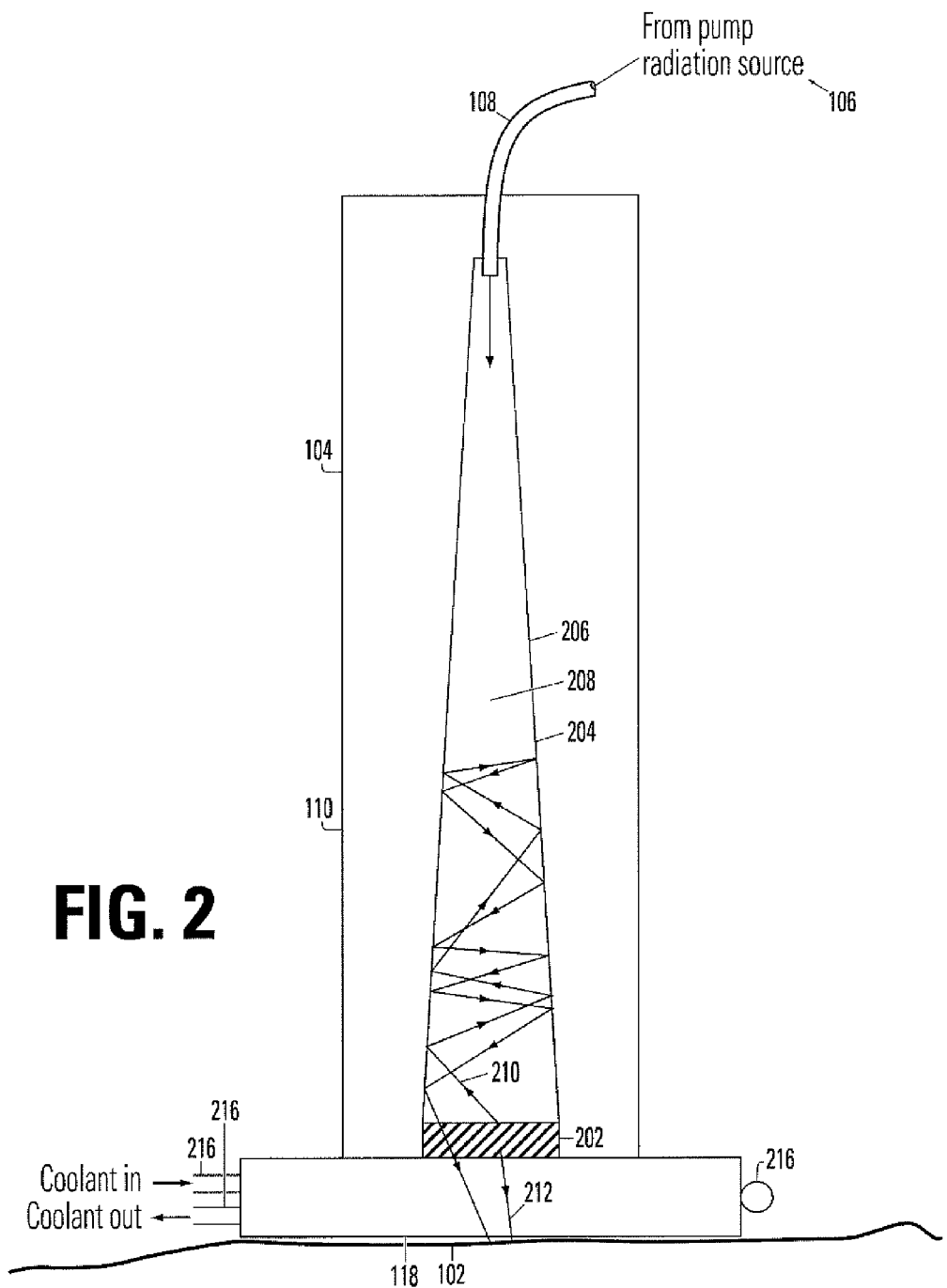
FIG. 2 is a cross-sectional view of a first embodiment of the fluorescent device.

Reference is now directed to FIG. 2, which shows a cross-sectional view of device 104. Device 104 includes housing 110 in which is disposed a fluorescent element 202. A redirector 204, which operates to redirect radiation emitted by fluorescent element 202 toward tissue target 102, includes a conically or frustro-conically shaped diffuse reflector 206 surrounding a cavity 208. One end of housing 110 is adapted to admit a corresponding end of optical fiber 108, which delivers the pump radiation from pump radiation source 106. Radiation leaving optical fiber 108 is thereafter directed through cavity 208 onto fluorescent element 202.

Fluorescent element 202 may be fabricated from any one of a number of materials having fluorescent properties. The fluorescent element material may be selected to provide desired spectral characteristics of the emitted fluorescent light. In one embodiment, fluorescent element 202 is fabricated from a solid material consisting of a fluorescent dye compound (also known as a fluorochrome), such as Rhodamine 6G dispersed in a polymeric matrix, such as polyvinyl toluene (PVT) or polymethyl methacrylate (PMMA, commonly known as Plexiglas). Those skilled in the art will recognize that materials of the foregoing description may be formed by dissolving or dispersing the fluorescent dye in a monomer prior to polymerization.

Other materials which may be used to fabricate fluorescent element 202 include, without limitation, a laser dye dispersed in the interstitial voids of porous glass (also known as "thirsty glass") or unconsolidated Vicor, phosphors, and laser crystals such as ruby. In still other implementations of the invention, fluorescent element 202 may comprise a static or recirculating encapsulated laser dye solution.

Figure 5:
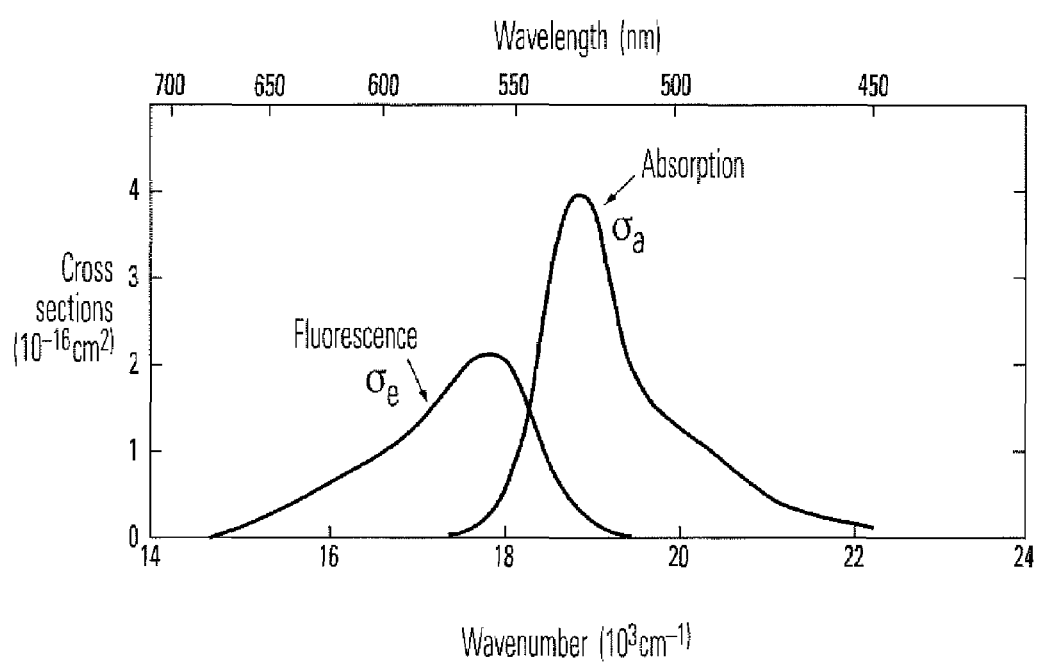
FIG. 5 depicts absorption and emission spectra of a representative fluorescent dye utilized in the fluorescent device.

As is depicted in FIG. 2, fluorescent element 202 may be constructed in a disk-like shape sized to be received within one end of housing 110 of device 104, although other geometries and configurations may be utilized without departing from the scope of the invention. Fluorescent element 202 is positioned to receive incident thereon the pump radiation delivered via optical fiber 108 At least a portion of the pump radiation is absorbed by fluorochromes (dye solution molecules) within fluorescent element 202. Absorption of the pump radiation results in excitation of the fluorochromes (i.e., boosting of an electron from a ground to an excited state). Excitation of fluorochromes causes fluorescent element 202 to emit radiation, the emitted radiation having substantially different spectral characteristics from those of the absorbed (pump radiation). Emission and absorption spectra of a representative fluorochrome are depicted in FIG. 5 and discussed below.

It will be recognized that fluorescent element 202 will emit radiation in all directions, and that in the absence of structures for redirecting radiation emitted by fluorescent element 202 in a non-preferred direction (i.e., away from tissue target 102), a substantial portion of the emitted radiation would be wasted. Device 104 is therefore provided with redirector 204 for redirecting toward tissue target 102 radiation emitted by fluorescent element 202 in a non-preferred direction such that substantially all of the radiation emitted by fluorescent element 202 reaches tissue target 102.

In the embodiment depicted in FIG. 2, redirector 204 comprises an elongated frustro-conically shaped diffuse reflector 206 surrounding cavity 208. The walls of reflector 206 are relatively widely spaced proximal to fluorescent element 202 and become progressively narrower in the direction extending away from fluorescent element 202. Radiation emitted by fluorescent element 202 in a non-preferred direction, as represented by ray 210, enters redirector 206 and undergoes multiple reflections from the walls of reflector 206 in a random-walk fashion. Ray 210 is eventually oriented such that it travels through cavity 208 in a direction substantially parallel to the central longitudinal axis of redirector 206 and subsequently passes through fluorescent element 202 and window 116 onto tissue target 102. Of course, radiation emitted by fluorescent element in a preferred direction (represented by ray 212) will travel directly from fluorescent element 202 to tissue target 102 through window 116. It is noted that redirector 206 may serve the additional function of collecting and redirecting toward tissue target 102 fluorescent radiation which is reflected by tissue target 102.

Those skilled in the art will recognize that redirector 206 may be constructed in other shapes (e.g., hemispherical), and hence the invention should not be construed as being limited to a conically- or frustro-conically shaped redirector.

Window 116 may be formed from glass, sapphire, or other suitable material which is substantially transparent in the wavelengths of the radiation emitted by fluorescent element 202. Window 116 terminates in a distal face 118 which is maintained in contact with tissue target 102 during operation of system 100. It has been found that undesirable collateral thermal damage caused to non-targeted tissue during procedures such as selective photothermolysis may be eliminated or substantially reduced by cooling the irradiated tissue (for a discussion of this benefit, reference may be made to U.S. Pat. No. 5,057,104 to Chess, entitled "Method and Apparatus for Treating Cutaneous Vascular Lesions"). To achieve cooling of tissue target 102, window 116 may be provided with thermally conductive tubing 216, arranged about the periphery of window 116, and through which is circulated chilled coolant supplied by coolant recirculation system 112. Tubing 216 may be held in good thermal contact with window 116 by means of an appropriate adhesive. Because glass or other optically transparent materials used to form window 116 typically have high thermal conductivities, cooling of window 116 effective cools tissue target 102 via conduction. Cooling of tissue target 102 may be optimized by applying a thermally conductive gel to tissue target 102 prior to bringing window 116 in contact therewith. Other techniques for cooling tissue target 102 are well known in the art and may be substituted for or used in conjunction with the technique described above.

Figure 3:
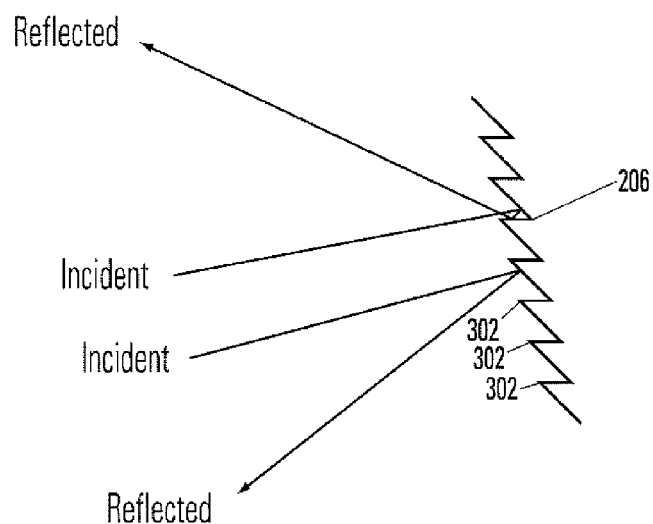
FIG. 3 depicts a fragmentary view of an exemplary reflective surface utilized in the fluorescent device.

FIG. 3 is a fragmentary view of a portion of a wall of reflector 206. Reflector 206 may be adapted with surface irregularities or protrusions 302 which effectively scatter light rays incident thereon, thus producing the random-walk behavior discussed above and depicted in FIG. 2. Various shapes and sizes of surface irregularities may be used to cause scattering. Reflector 206 may comprise a reflective coating deposited on a supporting substrate, or alternatively be directly machined from a block of metal or other reflective material.

Figure 4:
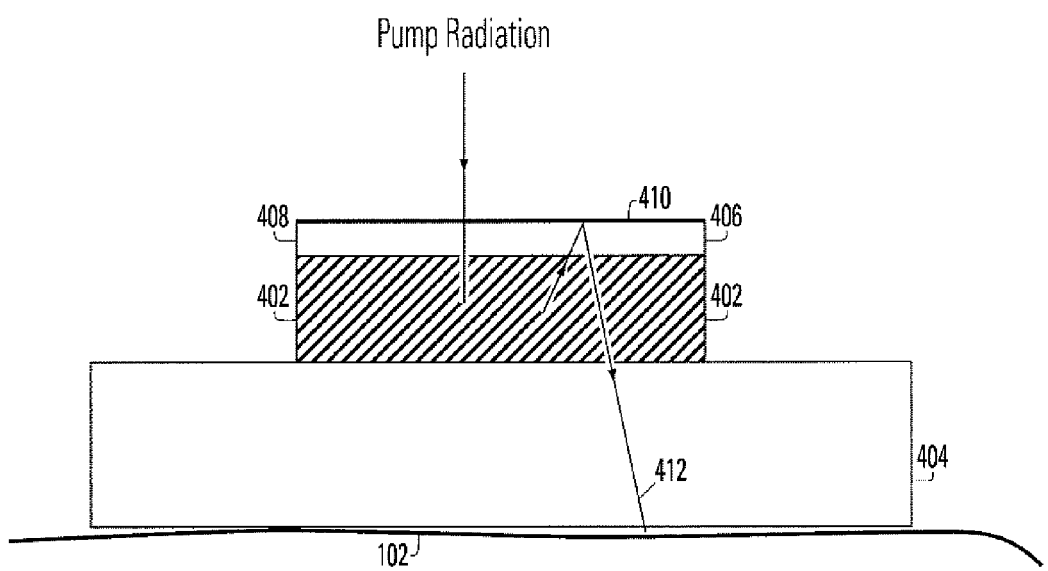
FIG. 4 is a cross-sectional view of a second embodiment of the fluorescent device.

FIG. 4 depicts a second embodiment of a device 400 for irradiating tissue 102. The device housing has been omitted in FIG. 4 for the purpose of clarity. Device 400 is provided with a fluorescent element 402 and window 404 of similar description to fluorescent element 202 and window 116 of the FIG. 2 embodiment. Redirector 406 consists essentially of a mirror 408 having a coating 410 which selectively reflects wavelengths corresponding to the radiation emitted by fluorescent element 402 while being substantially transparent to wavelengths corresponding to the pump radiation. Coating 410 may conventionally comprise a plurality of dielectric layers, the number, thicknesses, and composition of dielectric layers being chosen to produce the desired selective reflectance behavior. As indicated by ray 412, radiation emitted by fluorescent device 402 in a non-preferred direction (away from tissue target 102) is reflected by coating 410 and thereby redirected toward tissue target 102. Window 404 may be provided with cooling means as discussed above in connection with FIG. 2.

FIG. 5 depicts absorption and emission spectra of a representative fluorochrome (rhodamine 6G) which may be used in fluorescent element 202 or 402. It can be seen that the absorption spectrum exhibits a peak at approximately 530 nanometers, while the emission or fluorescence spectrum peaks at approximately 560 nanometers. The difference between the peaks of the absorption and emission spectra, called the Stokes shift, varies among different fluorochromes. A clinician may therefore match the emission spectra to the absorption characteristics of target tissue 102 by selecting a device having a fluorescent element which produces the desired Stokes shift.

Figures 6A, 6B:
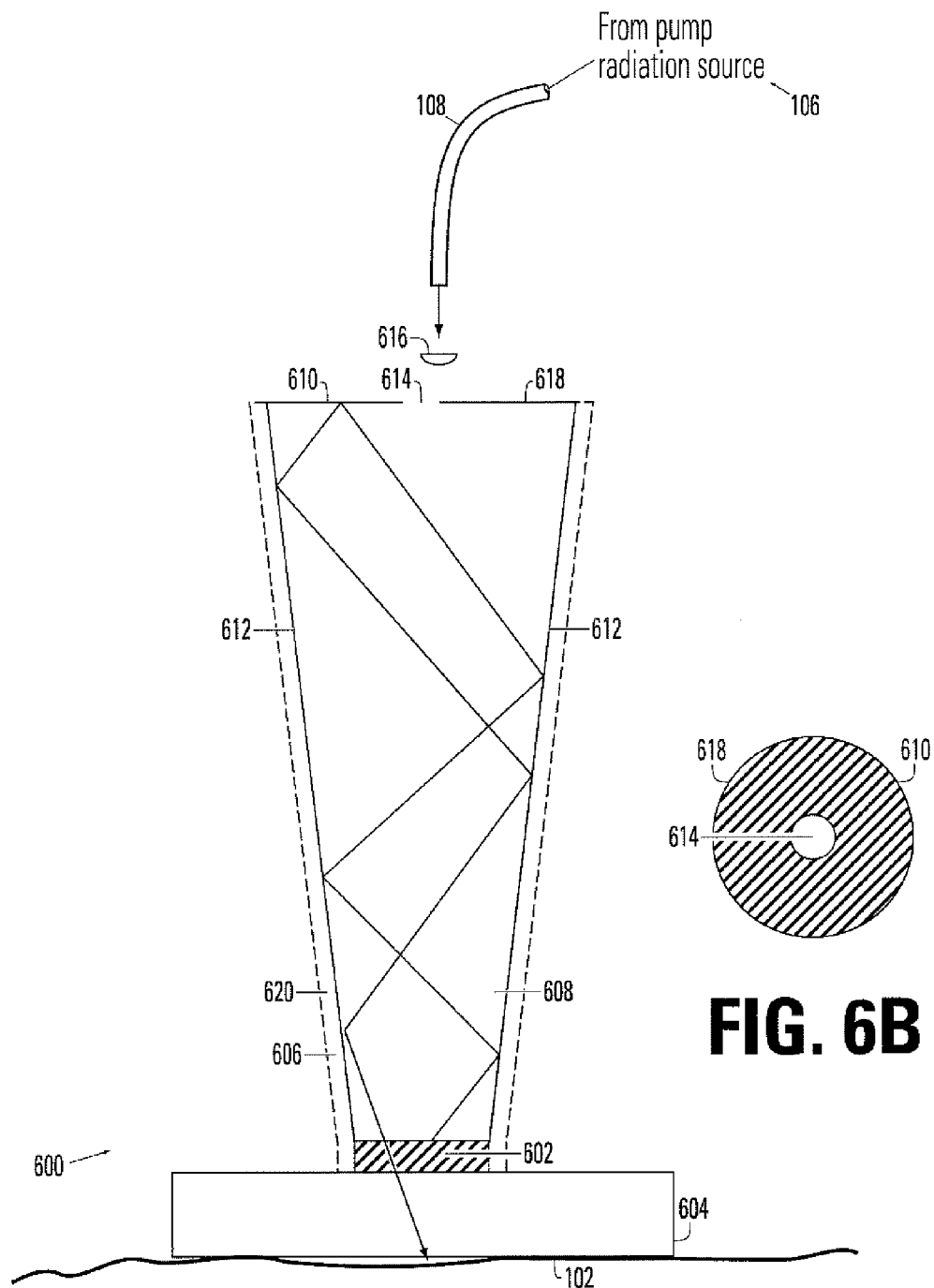
FIG. 6(*a*) is a cross-sectional view of a third embodiment of the fluorescent device.

FIG. 6(a) is a cross-sectional view of a device 600 for irradiating tissue 102 according to a third embodiment of the invention. Device 600 is provided with a fluorescent element 602 and window 604 of similar description to fluorescent element 202 and window 116 of the FIG. 2 embodiment. Redirector 606 comprises a waveguide 608 having a reflective entrance face 610 and reflective walls 612 extending from entrance face 610 to fluorescent element 602. The core of waveguide 608 may be fabricated from glass, sapphire or other suitable high refraction index material. Referring to FIG. 6(b), which shows a top plan view of entrance face 610, it is seen that entrance face 610 includes a central aperture 614 through which pump radiation from radiation source 106 is admitted into waveguide 608. Central aperture 614 is configured to be substantially transparent in the wavelength (s) of the pump radiation. Device 600 may include a divergent lens or similar element 616 positioned between the end of optical fiber 108 and aperture 614 to distribute the radiation emitted by fiber 108 over fluorescent element 602.

Entrance face 610 has an outer annular region 618 which is coated with a dielectric or metallic reflective coating to redirect toward tissue 102 radiation emitted by fluorescent element 602, as shown in FIG. 6(a). To minimize loss of emitted radiation through aperture 614, the area of aperture 614 is preferably a small fraction of the area of outer region 618. Walls 612 may also be provided with a dielectric or metallic reflective coating to redirect emitted radiation. However, in a preferred embodiment, walls 612 comprise a boundary between the core of waveguide 608 and a cladding 620 (depicted in phantom). Cladding 620 is constructed from a material, such as Teflon, having an index of refraction substantially lower than the index of refraction of the waveguide 608 core, which causes the emitted light to undergo total internal reflection at the boundary or walls 612. Radiation emitted by fluorescent element 602 in a non-preferred direction is thereby redirected toward tissue 102.

While waveguide 608 is depicted as having a downwardly tapering duct shape, it is not to be construed as limited thereto and may instead be constructed, for example, in a conical or cylindrical shape. Further, although waveguide 608 is shown as being circular in cross-section, polygonal and other cross-sectional shapes may be substituted.

It should be recognized that fluorescent devices of the foregoing description may be utilized for numerous therapeutic applications. Examples of therapies for which the devices may be advantageously employed include (without limitation) photothermolysis of vascular and pigmented lesions, tattoo removal, hair removal, and photodynamic therapy (PDT) for treatment of tumors.

While the invention has been particularly shown and described with reference to preferred embodiments thereof, it will be understood by those skilled in the art that various changes in form and details may be made therein without departing from the spirit and scope of the invention, as defined by the appended claims.

What is claimed is:

1. A method for irradiating tissue having absorption characteristics, comprising:
   directing pump radiation within a narrow spectral hand from a laser onto a fluorescent element;
   responsively generating radiation by spontaneous emission at the fluorescent element, the spontaneously emitted radiation being diffuse and having peak emission outside said narrow spectral band of the radiation, and at least a portion of which emitted radiation matches said absorption characteristics; and
   delivering at least a portion of the diffuse emitted radiation to a tissue target for treatment of said tissue, said portion having sufficient fluence for therapeutic effect.

2. The method of claim 1, wherein the step of directing incident radiation onto the fluorescent element includes directing incident radiation through an optical fiber.

3. The method of claim 1, wherein the step of delivering includes receiving a portion of the emitted radiation at a redirector; and
   redirecting the received portion of the diffuse emitted radiation by reflecting the emitted radiation from a diffuse reflector toward the tissue target.

4. The method of claim 1, wherein the step of delivering includes receiving a portion of the emitted radiation at a redirector; and
   redirecting the received portion of the diffuse emitted radiation by reflecting the emitted radiation from a reflective coating, the reflective coating being substantially transparent with respect to the pump radiation.

5. The method of claim 1, wherein the tissue target comprises a vascular lesion.

6. The method of claim 1, wherein the tissue target comprises a tumor.

7. The method of claim 1, wherein the tissue target comprises hair.

8. The method of claim 1, wherein the tissue target comprises a pigmented lesion.

9. The method of claim 1, further comprising the steps of cooling the tissue target.

10. The method of claim 9, wherein the step of cooling the tissue target comprises:
   providing a substantially transparent and thermally conductive window;
   placing a face of the window in thermal contact with the tissue target; and
   cooling the window.

11. A method for irradiating tissue having absorption characteristics, comprising:
   directing pump radiation onto a fluorescent element;
   responsively generating radiation by spontaneous emission at the fluorescent element, the spontaneously emitted radiation being diffuse and having spectral characteristics substantially different from the incident radiation, and at least a portion which emitted radiation matches said absorption characteristics;
   receiving a portion of the diffuse, spontaneously emitted radiation at a redirector; and
   redirecting the received portion of the emitted radiation toward a tissue target for treatment of said tissue, wherein the step of redirecting the emitted radiation includes reflecting the emitted radiation from the boundary between a waveguide core and cladding material, the cladding material having a substantially lower index of refraction than the waveguide core, said portion having sufficient fluence for therapeutic effect.

12. A device for irradiating tissue having absorption characteristics, comprising:
   a fluorescent element positioned to receive pump radiation from a laser having a narrow spectral band and responsively generate radiation by spontaneous emission, the spontaneously emitted radiation being diffuse and having peak emission outside said narrow spectral band, and at least a portion of which emitted radiation matches said absorption characteristics; and
   the fluorescent element delivering at least a portion of the diffuse emitted radiation toward a tissue target for treatment of said tissue, said portion having sufficient fluence for therapeutic effect.

13. The device of claim 12, wherein the fluorescent element comprises a fluorochromes dispersed in a solid medium.

14. The device of claim 13, wherein the fluorescent substance includes fluorescent ions, and the solid medium is selected from a group consisting of a solid-state crystal and a glass.

15. The device of claim 13, wherein the fluorescent substance includes a fluorescent dye, and the solid medium is selected from a group consisting of a polymer and a glass.

16. The device of claim 15, wherein the solid medium comprises a polymer selected from a group consisting of polymethyl methacrylate (PMMA) and polyvinyl toluene (PVT).

17. The device of claim 12, including a diffuse reflector for redirecting at least a portion of the diffuse emitted radiation toward the tissue target.

18. The device of claim 12, wherein the pump radiation is generated by a frequency-doubled solid-state laser.

19. The device of claim 12, wherein the pump radiation is delivered to the fluorescent element through an optical fiber.

20. The device of claim 12, wherein the pump radiation is delivered to the fluorescent element through an articulated arm.

21. The device of claim 12, including a reflective coating configured to reflect the emitted radiation toward the tissue target, the reflective coating being substantially transparent with respect to the pump radiation.

22. A device for irradiating tissue, comprising:
   a fluorescent element positioned to receive pump radiation having a narrow spectral band and responsively generate radiation by spontaneous emission, the spontaneously emitted radiation being diffuse and having peak emission outside said narrow spectral band; and
   the fluorescent element delivering at least a portion of the diffuse emitted radiation toward a tissue target, wherein the fluorescent element comprises a liquid fluorescent dye solution.

23. The device of claim 22, wherein the dye solution is static.

24. The device of claim 22, wherein the dye solution is continuously pumped through the fluorescent element.

25. A device for irradiating tissue, comprising:
   a fluorescent element positioned to receive pump radiation having a narrow spectral band and responsively generate radiation by spontaneous emission, the spontaneously emitted radiation being diffuse and having peak emission outside said narrow spectral band, the fluorescent element delivering at least a portion of the diffuse emitted radiation toward a tissue target; and
   a diffuse reflector for redirecting at least a portion of the diffuse emitted radiation toward the tissue target, wherein the diffuse reflector has a frustro-conical shape.

26. A device for irradiating tissue, comprising:
   a fluorescent element positioned to receive pump radiation having a narrow spectral band and responsively generate radiation by spontaneous emission, the spontaneously emitted radiation being diffuse and having peak emission outside said narrow spectral band, the fluorescent element delivering, at least a portion of the diffuse emitted radiation toward a tissue target; and
   a substantially transparent window having a proximal face positioned adjacent to the fluorescent element and a distal face for contacting the target.

27. The device of claim 26, further comprising means for cooling the window.

28. A device for irradiating tissue, comprising:
   a fluorescent element positioned to receive pump radiation and responsively generate radiation by spontaneous emission, the spontaneously emitted radiation being diffuse and having substantially different spectral characteristics with respect to the incident radiation; and
   a redirector for redirecting at least a portion of the diffuse, spontaneously emitted radiation toward a tissue target, wherein the redirector comprises a waveguide including a reflective entrance face and reflective walls, the entrance face having a substantially transmissive aperture formed therein for admitting pump radiation into the waveguide.

29. The device of claim 28, wherein the reflective walls comprise a boundary between a waveguide core having a relatively high index of refraction and a cladding material having a relatively low index of refraction, the boundary causing total internal reflection of a portion of the emitted radiation.

30. The device of claim 28, wherein the reflective walls comprise a reflective coating.

31. The device of claim 28, wherein the reflective walls comprise a metallic coating.

32. The device of claim 28, wherein the reflective walls comprises a dielectric coating.

33. A system for irradiating tissue having absorption characteristics, comprising:
- a pump radiation source for generating pump radiation from a laser having a narrow spectral band;
- a fluorescent element positioned to receive the pump radiation and responsively generate radiation by spontaneous emission, the spontaneously emitted radiation being diffuse and having peak emission outside said narrow spectral band, and at least a portion of which emitted radiation matches said absorption characteristics; and
- a redirector for redirecting at least a portion of the diffuse emitted radiation toward a tissue target for treatment of said tissue, said portion having sufficient fluence for therapeutic effect.

* * * * *